(12) United States Patent
Olguin Alvarez et al.

(10) Patent No.: US 10,146,890 B2
(45) Date of Patent: Dec. 4, 2018

(54) SIMULATION UPDATES THE DESIGN

(71) Applicant: Autodesk, Inc., San Rafael, CA (US)

(72) Inventors: Carlos Edel Olguin Alvarez, San Francisco, CA (US); Malte Sebastian Tinnus, Berkeley, CA (US); Florencio German Mazzoldi, Burnsville, MN (US)

(73) Assignee: Autodesk, Inc., San Rafael, CA (US)

( * ) Notice: Subject to any disclaimer, the term of this patent is extended or adjusted under 35 U.S.C. 154(b) by 527 days.

(21) Appl. No.: 14/839,781

(22) Filed: Aug. 28, 2015

(65) Prior Publication Data

US 2017/0060723 A1 Mar. 2, 2017

(51) Int. Cl.
*G06F 17/50* (2006.01)

(52) U.S. Cl.
CPC .......... *G06F 17/50* (2013.01); *G06F 17/5009* (2013.01)

(58) Field of Classification Search
USPC .................................. 703/2, 10, 20; 714/764
See application file for complete search history.

(56) References Cited

U.S. PATENT DOCUMENTS

| 9,451,051 | B1* | 9/2016 | Ray | H04L 67/38 |
| 2009/0094504 | A1* | 4/2009 | Sadakata | G06F 11/1032 714/764 |
| 2010/0153082 | A1* | 6/2010 | Newman | G01N 33/5008 703/11 |
| 2011/0208491 | A1* | 8/2011 | Ast | G06F 17/5009 703/2 |

\* cited by examiner

*Primary Examiner* — Thai Phan
(74) *Attorney, Agent, or Firm* — Womble Bond Dickinson (US) LLP

(57) ABSTRACT

A method and apparatus of a device that updates rules for a plurality of entities in a simulation as the simulation is running is described. In an exemplary embodiment, the device receives configuration parameters for the simulation, where the configuration parameters include a plurality of rules that control the interactions of the plurality of entities in the simulation. In addition, the device performs the simulation for a first plurality of iterations. Furthermore, the device analyzes the simulation results to determine if there is an update for the plurality of rules. If there is an update for the plurality of rules, the device creates the rule update for the plurality of rules. The device additionally applies the rule update to the plurality of rules.

20 Claims, 10 Drawing Sheets

SIMULATION UPDATES THE DESIGN

FIELD OF INVENTION

This invention relates generally to computational technology and more particularly to a simulation that updates a design of a system during the course of the simulation.

BACKGROUND OF THE INVENTION

A computer simulation is used to explore in silico how the real world works. For a simulation, the user defines the setup of the simulation and adds the rules the user knows about the relationship among the different "actors" in the simulation. For instance, in the case of coarse molecular simulations, the user may define a rule stating that a type of particle A is attracted to a type of particle B. The simulator would use these rules to define how particles of type A and B behave in the environment.

Many times, there are implicit rules present in the simulation. The user does not specify these implicit rules but these implicit rules can emerge from the simulation. For instance, geometric shapes or electrostatic forces for some particles may define that once they come close they would stick together. The user may not know this attraction exists before running the simulation. This invention allows those rules to emerge from the simulation and be reflected on the design.

SUMMARY OF THE DESCRIPTION

A method and apparatus of a device that updates rules for a plurality of entities in a simulation as the simulation is running is described. In an exemplary embodiment, the device receives configuration parameters for the simulation, where the configuration parameters include a plurality of rules that control the interactions of the plurality of entities in the simulation. In addition, the device performs the simulation for a first plurality of iterations. Furthermore, the device analyzes the simulation results to determine if there is an update for the plurality of rules. If there is an update for the plurality of rules, the device creates the rule update for the plurality of rules. The device additionally applies the rule update to the plurality of rules.

Other methods and apparatuses are also described.

BRIEF DESCRIPTION OF THE DRAWINGS

The present invention is illustrated by way of example and not limitation in the figures of the accompanying drawings in which like references indicate similar elements.

DETAILED DESCRIPTION

Figure 1:
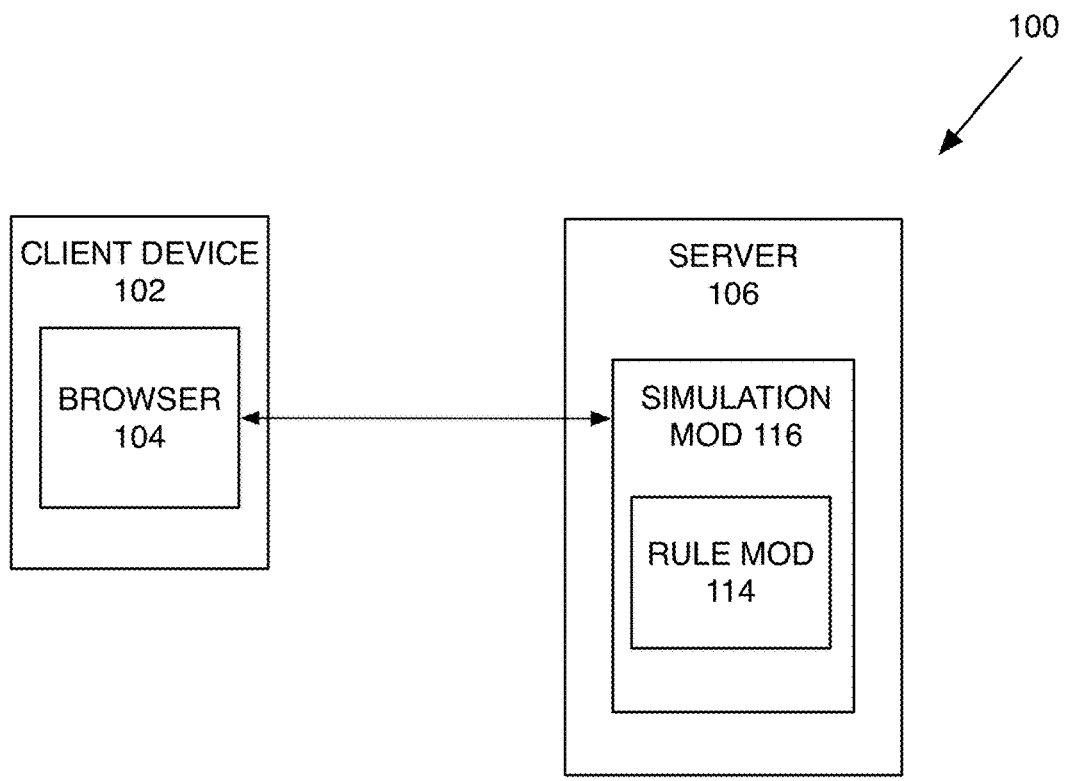
FIG. 1 is a block diagram of one embodiment of a system that computes a simulation and updates rules for that simulation to a client device.

A method and apparatus of a device that updates rules for a plurality of entities in a simulation as the simulation is running is described. In the following description, numerous specific details are set forth to provide thorough explanation of embodiments of the present invention. It will be apparent, however, to one skilled in the art, that embodiments of the present invention may be practiced without these specific details. In other instances, well-known components, structures, and techniques have not been shown in detail in order not to obscure the understanding of this description.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

In the following description and claims, the terms "coupled" and "connected," along with their derivatives, may be used. It should be understood that these terms are not intended as synonyms for each other. "Coupled" is used to indicate that two or more elements, which may or may not be in direct physical or electrical contact with each other, co-operate or interact with each other. "Connected" is used to indicate the establishment of communication between two or more elements that are coupled with each other.

The processes depicted in the figures that follow, are performed by processing logic that comprises hardware (e.g., circuitry, dedicated logic, etc.), software (such as is run on a general-purpose computer system or a dedicated machine), or a combination of both. Although the processes are described below in terms of some sequential operations, it should be appreciated that some of the operations described may be performed in different order. Moreover, some operations may be performed in parallel rather than sequentially.

The terms "server," "client," and "device" are intended to refer generally to data processing systems rather than specifically to a particular form factor for the server, client, and/or device.

A method and apparatus of a device that updates rules for a plurality of entities in a simulation as the simulation is running is described. In one embodiment, the device performs a simulation on a system with multiple entities using a set of rules that control the interactions of the multiple entities. In one embodiment, the set of rules is the design for the simulation. During the simulation, the device analyzes the results to determine if the rules used on the simulation can be updated. In one embodiment, the rules are updated if there are implicit relationships that are discovered during the course of the simulation. For example and in one embodiment, if during a simulation that simulates red and blue particles, the simulation reveals that blue particles are attracted to red particles, the device will add a rule stating that the blue and red particles are attracted to each other within that simulation system. In one embodiment, the rule can be added at the end of the simulation and be used for another simulation of the same type. In another embodiment, the device adds the rule to create a new set of rules during the simulation and the simulation continues running with the new set of rules.

In one embodiment, the device analyzes the simulation results for a new rule or rule update. The rule update can be an additional new rule (e.g., adding an attraction potential between the blue and red particles), modification of an existing rule (e.g., increasing or decreasing a potential), and/or deletion of an existing rule. In one embodiment, the device analyzes the simulation results to determine if two of the entities (e.g., particles, molecules, atoms, or other types of simulation units) spend a certain amount of time/iterations close together. In one embodiment, the device uses meta-rules to determine attraction, repulsions, or other rules that can be derived. If so, the device modules will derive a rule that the two entities have an attraction. Conversely, if two entities do not spend time/iterations close to each other, the device may add a rule that indicates these two entities have a repulsion (e.g., a negative attraction).

FIG. 1 is a block diagram of one embodiment of a system 100 that computes a simulation and updates rules for that simulation to a client device. In FIG. 1, a client device 102 provides input for a simulation to the server 106. The server 106 receives the input from the client device 102, performs the simulation, and outputs intermediate results to the client device 102. In one embodiment, the client device 102 or server 106 can independently be personal computer, laptop, server, mobile device (e.g., smartphone, laptop, personal digital assistant, music playing device, gaming device, etc.), and/or any device capable requesting and/or displaying a query. In one embodiment, each of the client device 102 and server 106 can independently be a physical or virtual device. Client device 102 further includes a browser 104. In one embodiment, the browser 104 is a web browser that is capable of making web requests to the server 106 and receiving results from those requests for display on the client device 102. In addition, the server 106 further includes a simulation module 116 for performing simulation (e.g., molecular dynamics, Monte Carlo, or other types of computer simulations of different natural systems in physics (computational physics), astrophysics, chemistry and biology, human systems in economics, psychology, social science, and engineering). In another embodiment, the simulations can be numerical simulations, stochastic simulations, statistical simulations, agent-based simulations, time stepped dynamic models, computational fluid dynamics, or other types of simulations. In this embodiment, the simulation module 116 further includes a rules module 114. In this embodiment, the rules module 114 analyzes the relationship between the molecules (or other entities) involved in a simulation being conducted by the multidimensional optimization module 108 to derive rules that describe relationships between the molecules (or other entities) that are being computed during the simulation. For example in one embodiment, if during a simulation, the simulation reveals that blue particles are attracted to red particles, the simulation module 106 will add a rule stating that the blue and red particles are attracted to each other within that simulation system. Discovering rules during the simulation is further described in FIGS. 2-5 below.

Figure 2:
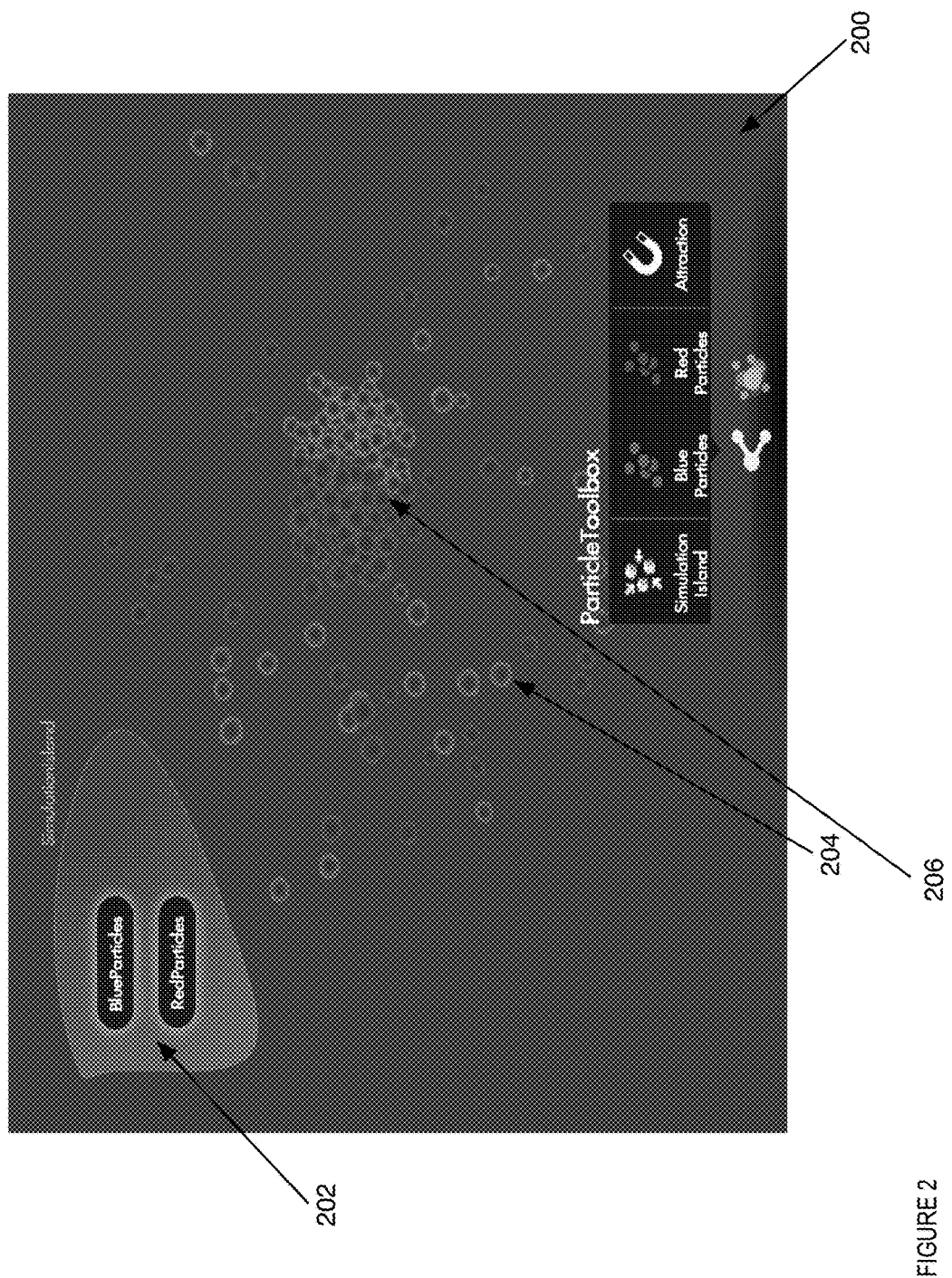
FIG. 2 is an illustration of one embodiment of a simulation island and a display of a result of the simulation for this island.

FIG. 2 is an illustration of one embodiment of a user interface 200 of a simulation island 202 and a display of a result of the simulation for this island. In FIG. 2, the user interface 200 includes the simulation island 202 and a display of the red and blue particles being simulated. In one embodiment, a simulation is set up to simulate a system of blue and red particles. In this embodiment, the type of simulation can be a type of calculation that allows the system to evolve over time (e.g., molecular dynamics, Monte Carlo, or another type of simulation as described in FIG. 1 above). The red and blue particles can be attractive or repulsive between each other or with themselves, depending on the type of potential or function used to model each particle in the simulation. Types of potentials that can be used are electrostatic potentials, Lennard-Jones potentials, and/or another type of potential). For example and in one embodiment, the blue particles can be attractive to each other and repulsive to the red particles, more attractive to the red particles than to other blue particles, or some other type of attraction or repulsion. In this example, the red particles may have the same or different potentials as the blue particles. In addition, the user interface 200 can include a user interface mechanism (not illustrated) to enter and edit the configuration parameters for the blue and red particles. In addition, the user interface can allow the user to enter the type of simulation (e.g., molecular dynamics, Monte Carlo, or other type of simulation), the simulation parameters (e.g., number of steps/iterations to take, starting forces, number of particles, or other types of parameters used for the simulation and meta-rules).

In one embodiment, the simulation island 202 is an environment that includes the components that are used for the simulation. In this embodiment, the blue 204A and red 204B particles are illustrated during the simulation. Some of these particles are clustered together 206 and other particles are not clustered. In this embodiment, the cluster of read and blue particles 206 illustrates that the blue and red particles have an attraction for each other and will tend to cluster together. While in FIG. 2, a simple simulation of red and blue particles is illustrated, in alternate embodiments, a more complicated system can be used, such as a protein solvated in water with one or more target molecules. In this embodiment, which target molecules are attracted or repulsed by the active sites of the protein may not be self-evident.

Figure 3:
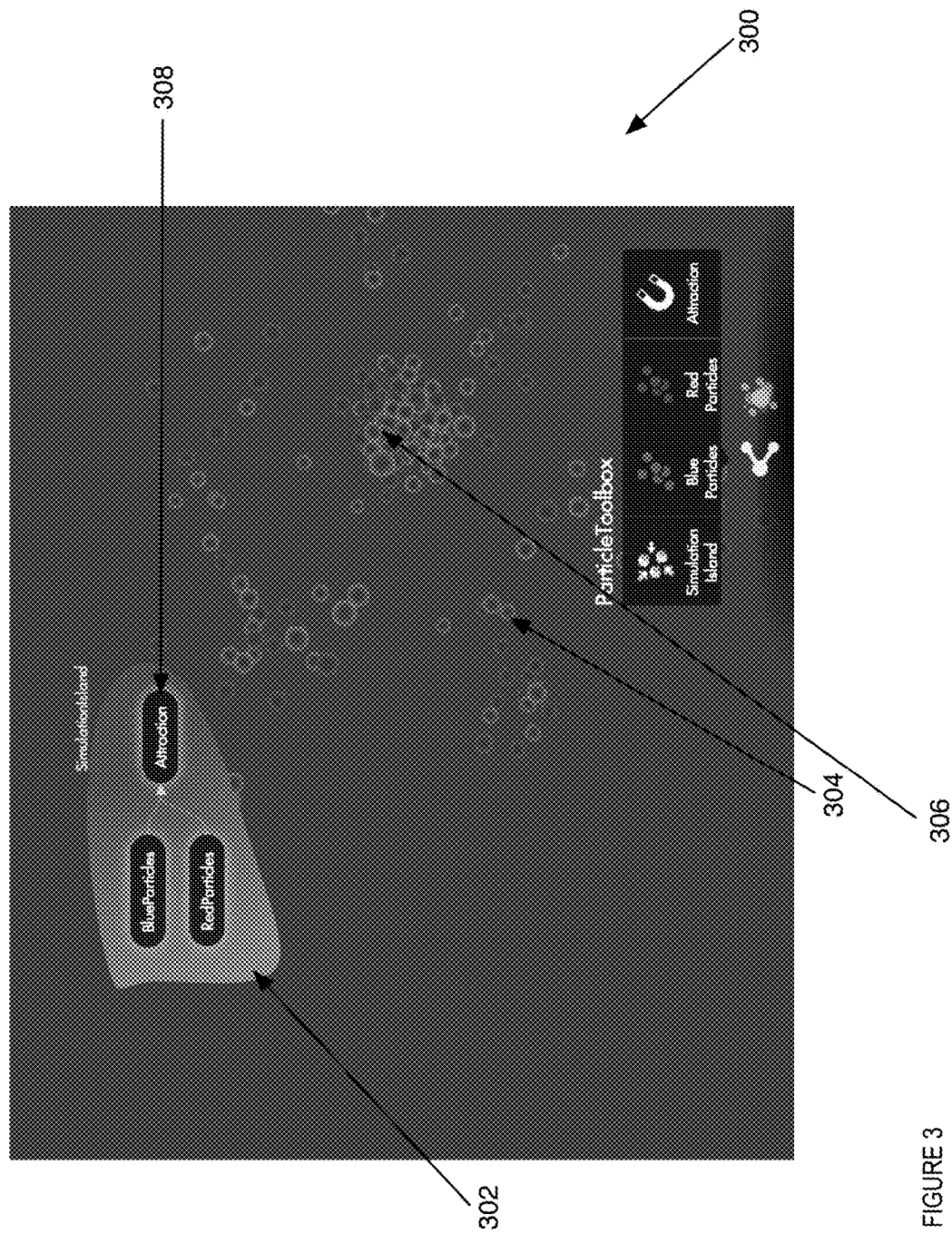
FIG. 3 is an illustration of one embodiment of a simulation island and a display of a result of the simulation for this island, where the simulation island determines an additional rule for this island.

In FIG. 2, one result from the simulation was that the blue and red particles have an attraction that may be greater than the self-attraction for each of the particles. FIG. 3 is an illustration of one embodiment of a user interface 300 of a simulation island 302 and a display of a result of the simulation for this island, where the simulation island 302 includes an additional rule for this island. In FIG. 3, the user interface 300 includes a simulation island 302 and a display of the red 304A and blue 304B particles being simulated. In one embodiment, the simulation island includes an extra rule 308 for an attraction between the red 304A and blue 304B particles. In this embodiment, this extra rule 308 represents the attraction between the red 304A and blue 304B particles. In one embodiment, the system conducting the simulation derives this rule by analysis of the simulation. In this embodiment, the rules module of a simulation module analyzes the different iterations of the simulations to derive rules from the simulation. In this embodiment, the rules module determines if two entities (e.g., particles, molecules, atoms, or other types of simulation units) spend a certain amount of time/iterations close together, the rules modules will derive a rule that the two entities have an attraction. In one embodiment, the user defines meta-rules that control the rule creation. For example and in one embodiment, the user may specify "If 30% of the some particles have been in contact with other type of particles during more than 50 time periods, add the attraction rule for these particles." Conversely, if two entities do not spend time/iterations close to each other, the rules module may add a rule that indicates these two entities have a repulsion (e.g., a negative attraction).

In this embodiment, the system being illustrated is a simple 2-particle type system simulation. However, in alternate embodiments, with a more complicated system, deriving rules for attractions and/or repulsions may not be straightforward. For example and in one embodiment, if there is a N component system, where one of the components is a solvent (e.g., water), one component is a protein with one or more active sites, and components 3-N are other types of molecules (e.g., different target molecule(s)), there may not be a specific attraction rules initially configured between the components 3-N and the protein's active sites. During the simulation, the rules modules determines that one component sticks to one of the protein active sites and does not leave, another component sticks and comes off another protein active site, and a third component does not get close to any of the protein active sites. In this example, the rules module would determine a strong attraction for the first component with this protein active site, a mild attraction between the second component and the corresponding protein active site, and a repulsion between the third component and the protein active sites. For example and in one embodiment, a user may add a meta-rule that specifies "If 30% of the first component have been in contact with a corresponding protein active site for more than 50 tics, add the attraction rule.

Figure 4:
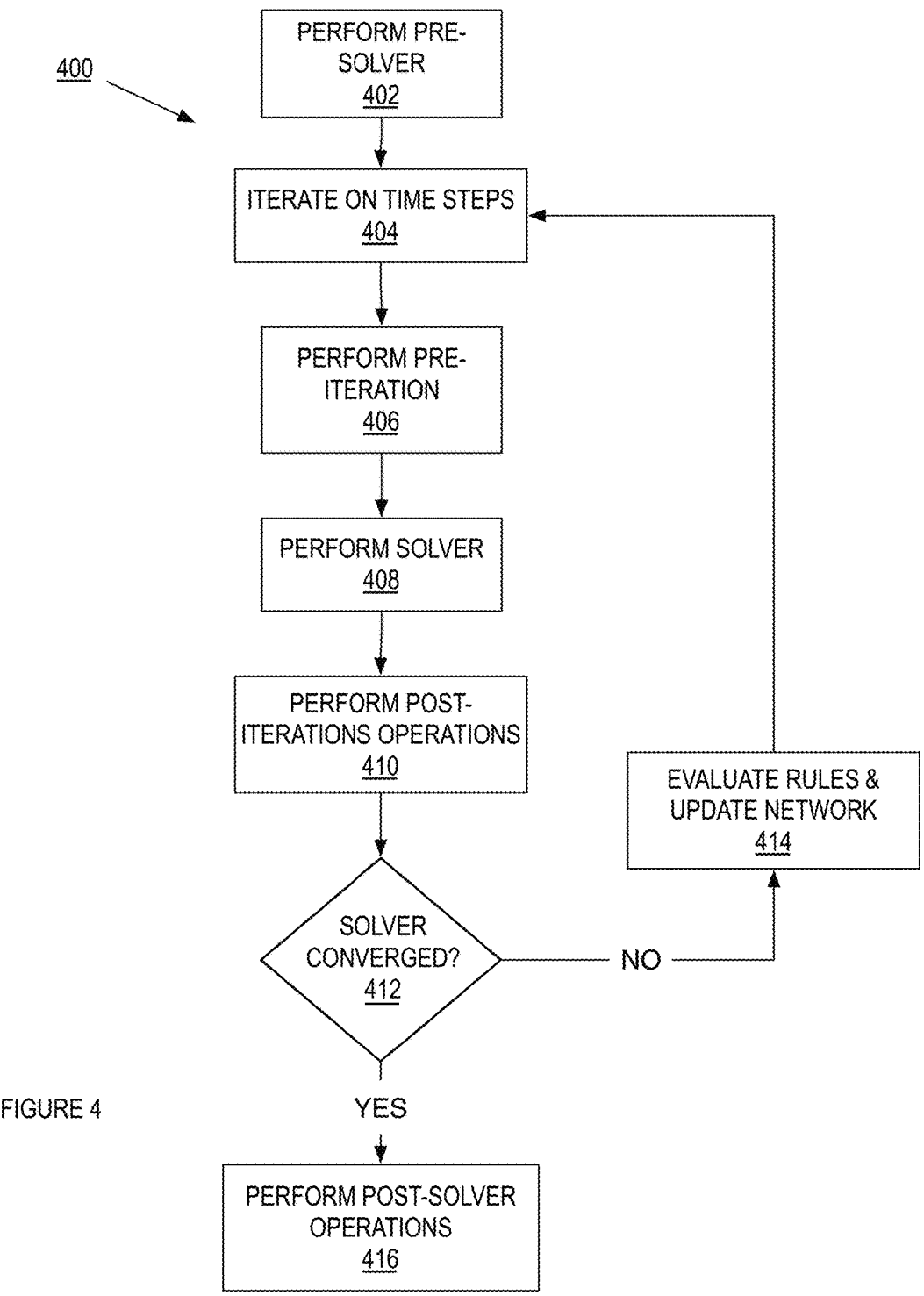
FIG. 4 is a flowchart of one embodiment of a process that updates the rules used for a simulation based in the results of the simulation.

As described above, as a simulation is running, the simulation module can analyze the simulation results during the simulation and add, modify, and/or delete rules used for the simulation. FIG. 4 is a flowchart of one embodiment of a process 400 that updates the rules used for a simulation based on the results of the simulation. In one embodiment, a rules module performs process 400 to update rules used for a simulation based in the results of the simulation, such as rules module 114 as described in FIG. 1 above. In FIG. 4, process 400 performs a pre-solver at block 402. In one embodiment, the pre-solver sets up the simulation. For example and in one embodiment, the pre-solver populates the simulation system with the particles that are being simulated. At block 404, process 400 iterates the simulation for N time steps or iterations. For example and in one embodiment, process 400 can iterate the simulation for 100 time steps. Process 400 performs a pre-iteration at block 406. In one embodiment, the pre-iteration initializes the data structures for the iteration. For example and in one embodiment, if process 400 uses a data structure to hold the velocities of all the particles in the simulation, the pre-iteration creates this data structure and initializes the values for the data structure. At block 408, process 400 performs the solver. In one embodiment, the solver is a step in which process 400 determines the next solution(s) to be used in the simulation for the simulation. In one embodiment, if the simulation is a molecular simulation, process 400 determines the next position and forces for the particles or molecules in the simulations. In another embodiment, if the simulation is a different type of simulation, process 400 performs a type of solver corresponding to the type of simulation.

At block 410, process 400 performs post-iterations operations at block 410. In one embodiment, the post-iteration updates the data structures of the overall scene based on the results of the solver. At block 412, process 400 determines if the solver has converged. In one embodiment, process 400 determines if the solver converges by determining if the solver has reached a threshold. If the solver has converged, process 400 performs post-solver operations at block 410. In one embodiment, the post-solver operations clean up the data structures from the simulation and package the simulation information.

If the solver has not converged, process 400 evaluates the rules of the simulation and updates the network. In one embodiment, process 400 determines if a pair of components of the simulation has spent enough time (or iterations) close to each other. If so, process 400 can add an attraction rule to the simulation island for this component pair. Alternatively, if process 400 determines that if a pair of components of the simulation does not approach each other, process 400 can add a repulsion rule for this component pair. Furthermore, instead of adding a new rule, process 400 can modify an existing rule, such as increasing or decreasing an attraction or repulsion rule. In one embodiment, for each new rule (or rule update), process 400 adds these new rules or rule updates to the network of rules used in the simulation island. Execution proceeds to block 404 above.

Figure 5:
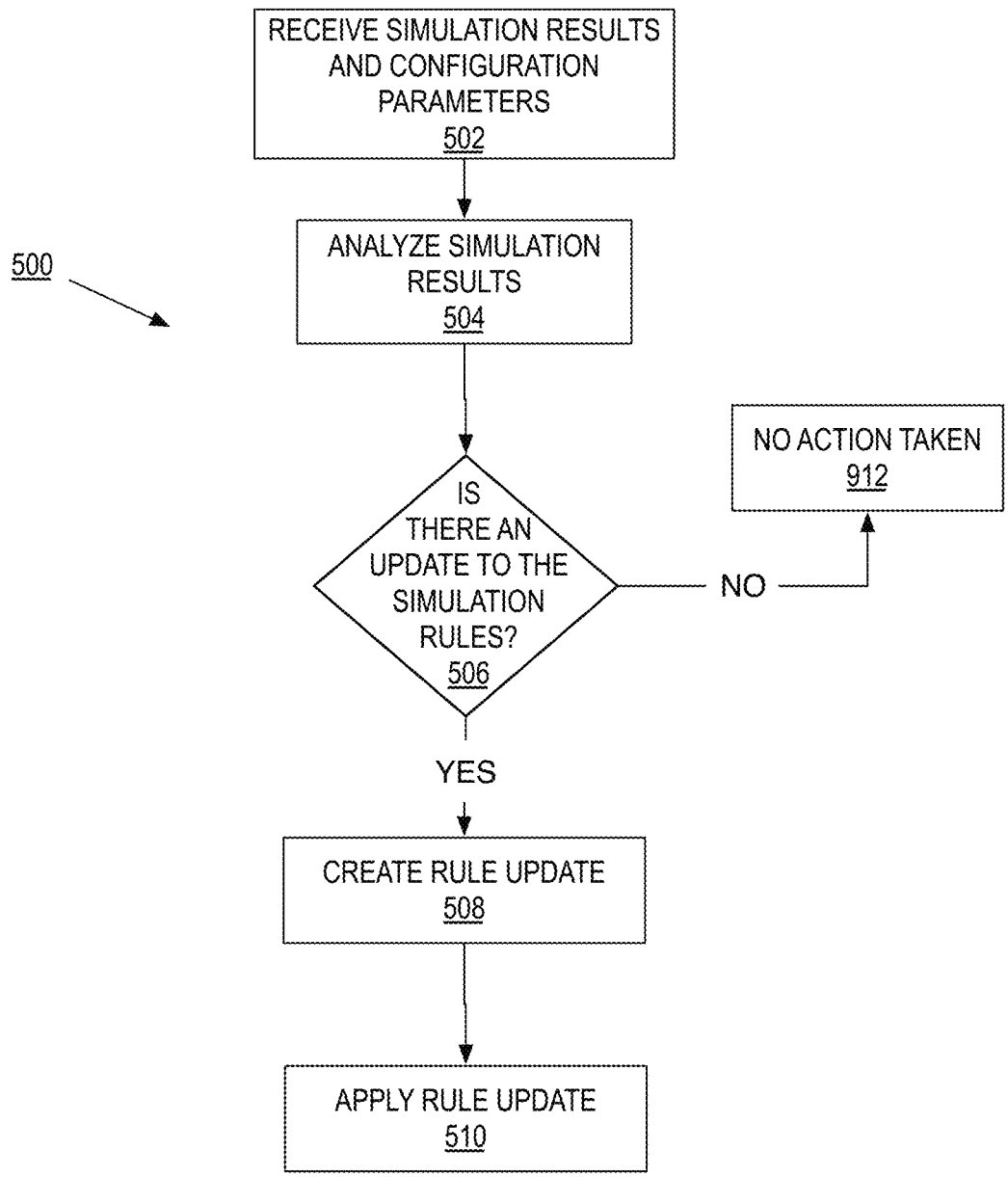
FIG. 5 is a flowchart of one embodiment of a process that analyzes the simulation results for rule updates and generates the rule update.

FIG. 5 is a flowchart of one embodiment of a process 500 that analyzes the simulation results for rule updates and generates the rule update. In one embodiment, process 500 is performed by a rules module to analyze the simulation results for rule updates and generate the rule update, such as the rules module 114 as described in FIG. 1 above. In FIG. 5, process 500 begins by receiving simulation results and configuration parameters at block 502. In one embodiment, the simulation results are the results generated by the simulation at each iteration computed by the simulation. For example and in one embodiment, the simulation results for each iteration can be entity positions, entity forces, velocity, acceleration, deformation, or another type of simulation result.

At bock 504, process 500 analyzes the simulation results for possible rule updates. In one embodiment, process 500 performs this analysis to determine if one or more of the entities are clustered with other entities for an extended period of time (or iterations). In this embodiment, two of the entities are clustered if these two entities are within an interaction distance of each other for a minimum number of iterations (e.g., time steps, or another type of iteration). In one embodiment, an interaction distance for an entity pair of atoms is within the combined van der Waal radii of the atom pair. In another embodiment, the interaction distance metric can be defined differently. In another embodiment, the minimum number of iterations can be determined from the meta-rules for the simulation island. For example and in one embodiment, if the two entities are a target molecule and a protein with an active site, if the target molecule is within the active site for more than one microsecond (e.g., 1000 iterations of one nanoseconds time steps), process 500 would determine this interaction is a candidate for a rule update. In this example, process 500 determines that the target molecule and the protein active site have an attraction that can be used for a new rule. If there is not a rule update, at block 512, no action is taken, as there is no update needed for the simulation rules.

If there is a rule update, at block 508, process 500 creates the rule update. In one embodiment, the rule update can be an addition of a new rule, a modification of an existing rule, or a rule deletion. For example and in one embodiment, using the example from above of the target molecule and protein active site, a rule update can be adding a new rule that creates an attraction potential between the target molecule and protein active site. In another example, if a target molecule is repulsed (e.g. does not come within contact with the protein active site) with a protein active site, process 500 could create a repulsion potential between the target molecule and the protein active site. If throughout the simulation, it is clear that the attraction previously defined is not as strong as stated, process 500 would update the attraction rule to a weaker value. At block 510, process 500 applies the rule update.

Figure 6:
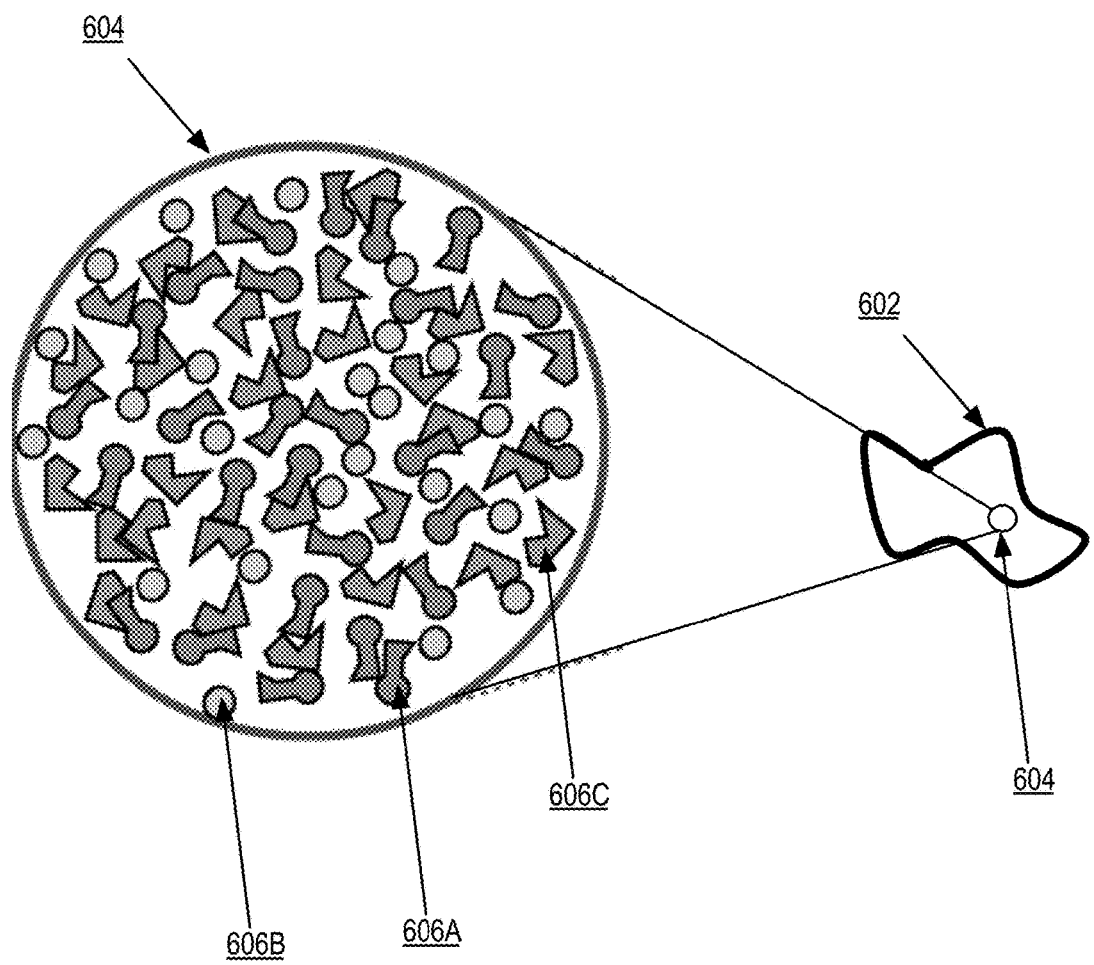
FIG. 6 is an illustration of one embodiment of a simulation system of yellow, red, and blue molecules.

FIG. 6 is an illustration of one embodiment of a system 602 of red, yellow, and blue molecules. In FIG. 6, a system of 602 is simulated with red 606A, yellow 606B, and blue 606C molecules using a simulation island as described in FIG. 2 above. In one embodiment, the different molecules 606A-C are distributed in the simulation. A portion 604 of the system is shown in FIG. 6, illustrating the distribution of the red 606A, yellow 606B, and blue 606C molecules. In one embodiment, data harvested from the simulation can also come from many simulation approaches in parallel including reality capture (e.g., experimental data, not necessarily simulation data). In one embodiment, this is called as in-matter computation as opposed to in silico computation. For example and in one embodiment, the amount of time red and blue molecules stay together in average is used to help define the dissociation constant $K_d$ value (or the $K_m$ value in the cases of an enzymatic reaction). In this example, this raw value information is passed upstream to a rules module (e.g. time together, number of collisions, and/or other types of information).

Figure 7A:
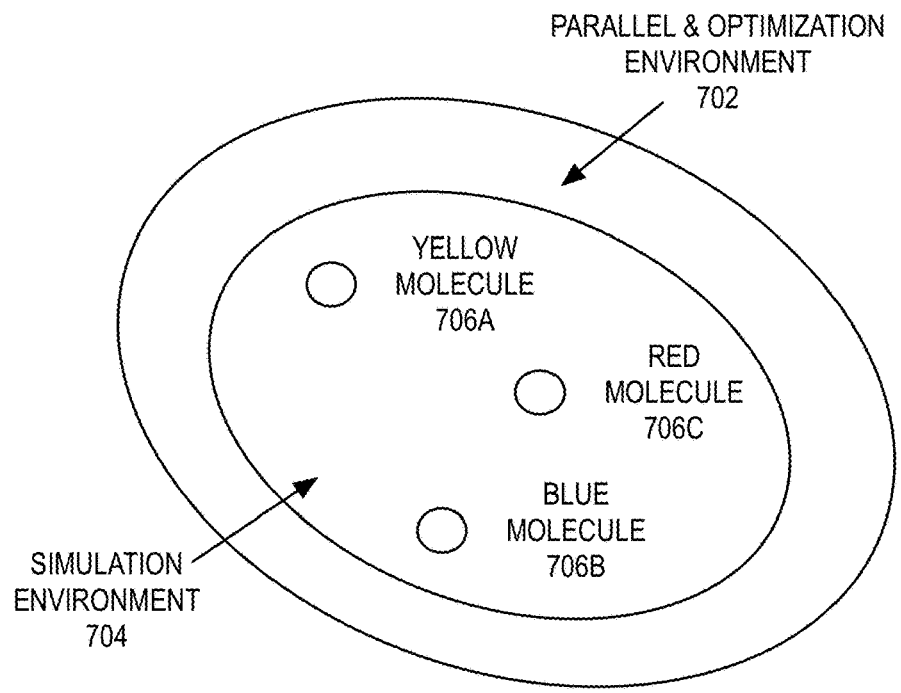
FIGS. 7A-B are illustrations of a simulation island for simulating the yellow, red, and blue molecules.
Figure 7B:
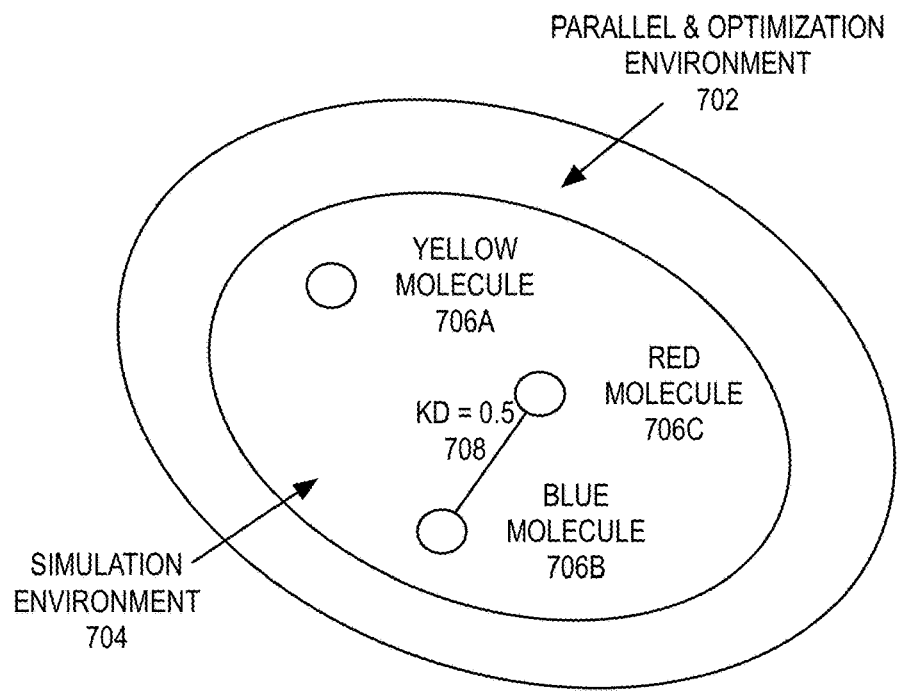

FIGS. 7A-B are illustrations of a simulation island 700 for simulating the yellow, red, and blue molecules. In FIG. 7A, and in one embodiment, the simulation island 700 is an abstraction of a many-to-one node relationship. In this embodiment, the simulation island 700 includes a parallelization and optimization environment 702, where the parallelization and optimization environment 702 includes a simulation environment 704. The simulation environment 704 further includes the different molecules: yellow molecules 706A; blue molecules 706B; and red molecules 706C. In one embodiment, the optimization could be seen as a higher island on top of lower islands applying pressure points on certain nodes and edges in order to drive the values of the next iteration in the design. In another embodiment, a simulation can be in a higher island on top of lower islands as described above.

In one embodiment, the simulation raw data can be used to derive rules. In FIG. 7B, the simulation island 700 includes the same environments as illustrated in FIG. 7A. In addition, the simulation includes a rule that is derived from the raw data of the simulation, which is a dissociation constant, $K_d$, between the blue and red molecules 706B-C with a value of $K_d$=0.5. In one embodiment, the correlation and casualty data across nodes is computed and fed into the creation of models describing the simulated system (the final model is the 'design' that now becomes more complete). In one embodiment, which equations to use are derived from the simulations results. In this embodiment, these equations can be unknown or they can represent a set of candidate equations defined based on the domain of practice or other input set by the user. For example and in one embodiment, the candidate equations for computing a kinetics constant the dissociation constant equation (1), $K_d$, $$K_d = \frac{[A]^x[B]^y}{[A_xB_y]} \quad (1)$$

and the Michaelis-Menten kinetics equation (2), $$v = \frac{d[P]}{dt} = \frac{V_{max}[S]}{K_M + [S]} \quad (2)$$

In one embodiment, if no equations were known a priori for the simulation, one approach could be to correlate the nodes in the graph in an increasingly inclusive fashion. For example, and in one embodiment, the nodes are initially correlated with each other in a matrix using something similar to the calculation of $K_d$. In one embodiment, this correlation is to determine if there is a dissociation constant equation relationship for the each of the molecules. For example and in one embodiment, the simulation determines if there are dissociation constant equation relationships for the yellow, red, and blue molecules. In another embodiment, the simulation can further expand the correlation to sets of three nodes. In this embodiment, the correlation can be the same or different type of correlation. For example and in one embodiment, the correlation attempted can be an enzymatic reaction, or a simpler type of correlation. In one embodiment, this type of analysis goes up in the order of correlated nodes (e.g., intra-molecule, pairwise inter-molecule, etc.). In this embodiment, a change in a parameter within the simulation (layer below) creates an additional simulation with that new value now being used, and a new correlation matrix needs to be computed. For example and in one embodiment, a change in the simulation will produce new results, such as new emergent or updated phenomena from which new rules could be derived according to that new simulation setup.

In one embodiment, the optimization layer on top of lower island(s) needs to account for the changes in the system as the optimization evaluates possible solutions against the design goals. In this embodiment, the possible solutions are derived from a multidimensional analysis entailed in evaluating the simulation parameters that were set to be explored across a range of values according to a particular search criteria or algorithm. For example and in one embodiment, imagine that a scientist decided to include a scenario where a small but non-negligible value for gravity seen as a force vector going down and applied to all particles. Since the scientist is not discarding the original scenario with zero gravity she now has two sets of data assuming everything else equal.

This may create additional computation but this type of computation is highly parallelizable. In this embodiment, this is where computation 'in matter' (meaning harvesting 'simulation' data from reality capture) could play an important role in at least creating a baseline model that is then tweaked in simulation. In one embodiment, a scientist may run an analysis in a multi-well plate (e.g. a 96 well plate, or a well plate with more or less plates) to measure the concentration of a certain molecule of interest. In this embodiment, the multi-well plate can be thought of as a 'physical' simulation. Here the physics engine is nature itself and not a solver that approximates it. The physical simulation may still be an approximation of what the scientist would actually want to determine at the end (e.g., a drug to be ingested by a human, so the human 'environment' would be different than the 96 well plate). In one embodiment, the idea is about merging these two types of 'simulations' by playing to the strengths of each and coming up with a more comprehensive approach toward converging to a certain design goal or set of goals. In this embodiment, this can be seen as a kind of meta-optimization since the overall approach also evaluates how much computation to allocate in a pipeline of in silico, in-vitro, in/ex-vivo, and/or other computation modules. For example and in one embodiment, in the very early beginning of an exploration scientist may chose to allocate more resources for an in silico computation to explore roughly (e.g., with ultra coarse grained simulations) a very large solution space that would be practically impossible to test in vitro under the same conditions (here, for example, only a very small sample could be synthesized and tested in vitro for basic cross-validation). In this embodiment, by using the simulations to narrow the scope of the problem, once the parameters of the simulation are better defined, the scientist can test some or all of the simulated solution space in vitro in a 96 well plate (or larger/smaller well plate, such as in a 10,000 well plate). In one embodiment, even with a large number well plate, the experimental data could be a small part of the simulation solution space. Thus, getting quantitative experimental data could be practically impossible to obtain than in an in-silico simulation. How much computation a scientist allocates for each step in the pipeline on each full cycle does not need to be decided by a human but could be the subject of analysis by the overarching optimization layer hence this could be seen as a form of meta-optimization.

Figure 8:
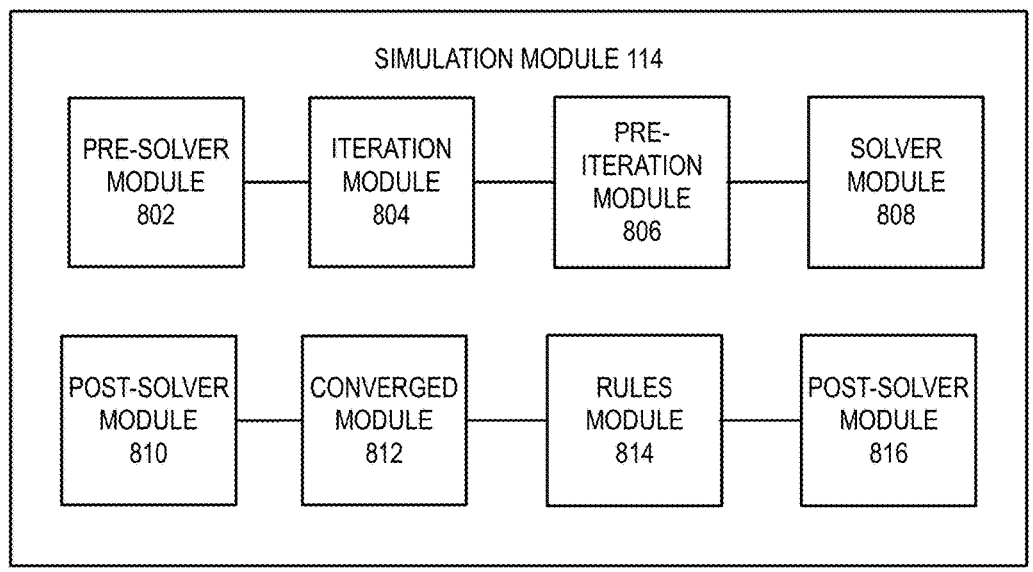
FIG. 8 is a block diagram of one embodiment of a simulation module that updates the rules used for a simulation based in the results of the simulation.

FIG. 8 is a block diagram of one embodiment of a simulation module 114 that updates the rules used for a simulation based in the results of the simulation. In one embodiment, the simulation module 114 includes pre-solver module 802, iteration module 804, pre-iteration module 806, solver module 808, post-solver module 810, converged module 812, rules module 814, and post-solver module 816. In one embodiment, the pre-solver module 802 performs the pre-solver function as described in FIG. 4, block 402 above. The iteration module 804 iterates on the time steps as described in FIG. 4, block 404 above. The pre-iteration module 806 performs the pre-iteration function as described in FIG. 4, block 406 above. The solver module 808 performs the solver function as described in FIG. 4, block 408 above. The post-solver module 810 performs the post-solver function as described in FIG. 4, block 410 above. The converged module 812 determines if the solver has converged as described in FIG. 4, block 412 above. The rules module 814 evaluates the rules and updates the network as described in FIG. 4, block 414 above. The post-solver module 816 performs post-solver function as described in FIG. 4, block 416 above.

Figure 9:
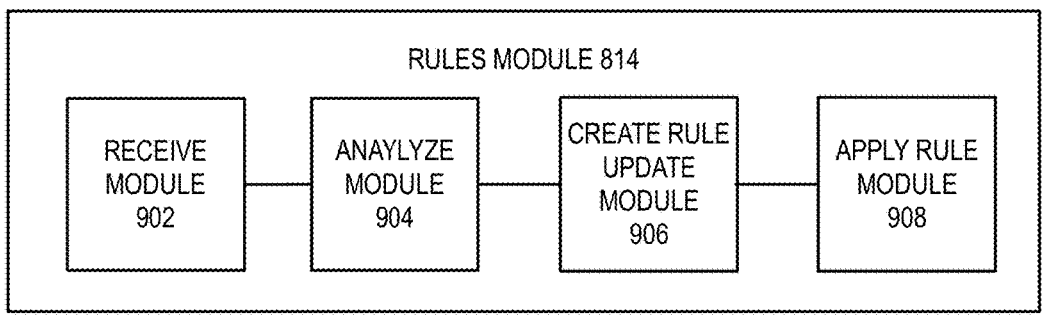
FIG. 9 is a block diagram of one embodiment of a rules module that updates rules using the simulation results.

FIG. 9 is a block diagram of one embodiment of a rules module 614 that updates rules using the simulation results. In one embodiment, the rules module 614 includes a receive module 902, analyze module 904, create rule update module 906, and apply rule module 908. In one embodiment, the receive module 902 receives the simulation results and configuration parameter as described in FIG. 5, block 502 above. The analyze module 904 analyzes the simulation results as described in FIG. 5, block 504 above. The create rule update module 906 creates a rules update as described in FIG. 5, block 508 above. The apply rule module 908 applies the rule update as described in FIG. 5, block 510 above.

Figure 10:
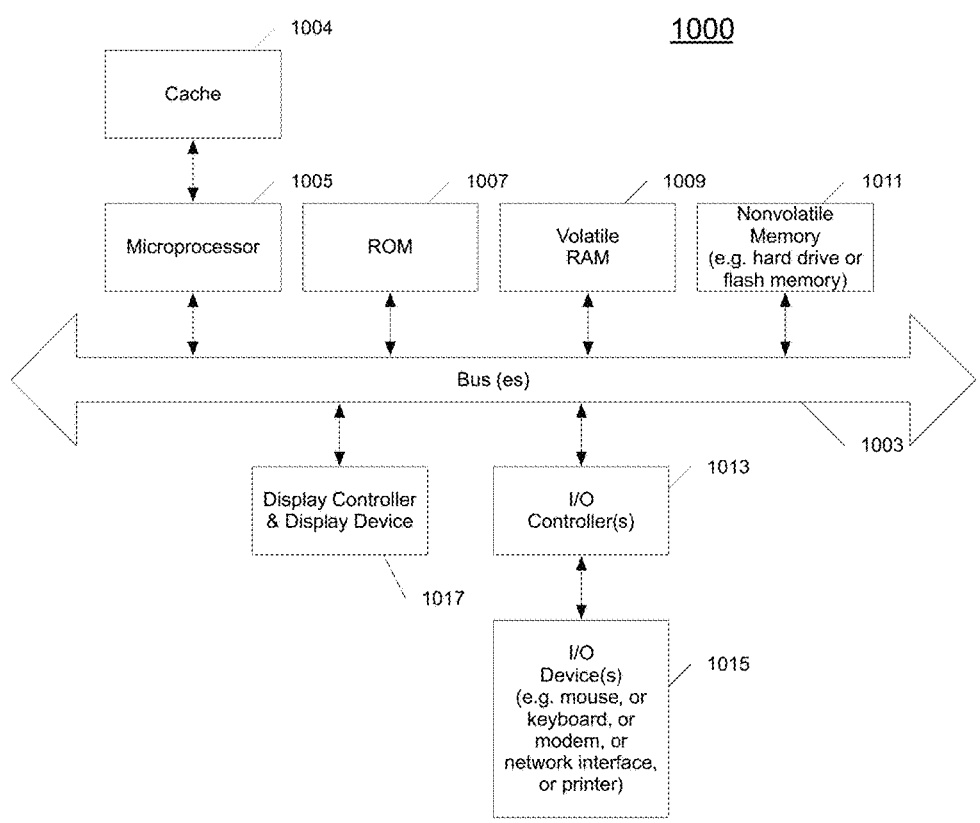
FIG. 10 illustrates one example of a typical computer system, which may be used in conjunction with the embodiments described herein.

FIG. 10 shows one example of a data processing system 1000, which may be used with one embodiment of the present invention. For example, the system 1000 may be implemented including a client device 102 or server 106 as shown in FIG. 1. Note that while FIG. 10 illustrates various components of a computer system, it is not intended to represent any particular architecture or manner of interconnecting the components as such details are not germane to the present invention. It will also be appreciated that network computers and other data processing systems or other consumer electronic devices, which have fewer components or perhaps more components, may also be used with the present invention.

As shown in FIG. 10, the computer system 1000, which is a form of a data processing system, includes a bus 1003 which is coupled to a microprocessor(s) 1005 and a ROM (Read Only Memory) 1007 and volatile RAM 1009 and a non-volatile memory 1011. The microprocessor 1005 may include one or more CPU(s), GPU(s), a specialized processor, and/or a combination thereof. The microprocessor 1005 may retrieve the instructions from the memories 1007, 1009, 1011 and execute the instructions to perform operations described above. The bus 1003 interconnects these various components together and also interconnects these components 1005, 1007, 1009, and 1011 to a display controller and display device 1013 and to peripheral devices such as input/output (I/O) devices which may be mice, keyboards, modems, network interfaces, printers and other devices which are well known in the art. Typically, the input/output devices 1015 are coupled to the system through input/output controllers 1013. The volatile RAM (Random Access Memory) 1009 is typically implemented as dynamic RAM (DRAM), which requires power continually in order to refresh or maintain the data in the memory.

The mass storage 1011 is typically a magnetic hard drive or a magnetic optical drive or an optical drive or a DVD RAM or a flash memory or other types of memory systems, which maintain data (e.g. large amounts of data) even after power is removed from the system. Typically, the mass storage 1011 will also be a random access memory although this is not required. While FIG. 10 shows that the mass storage 1011 is a local device coupled directly to the rest of the components in the data processing system, it will be appreciated that the present invention may utilize a non-volatile memory which is remote from the system, such as a network storage device which is coupled to the data processing system through a network interface such as a modem, an Ethernet interface or a wireless network. The bus 1003 may include one or more buses connected to each other through various bridges, controllers and/or adapters as is well known in the art.

Portions of what was described above may be implemented with logic circuitry such as a dedicated logic circuit or with a microcontroller or other form of processing core that executes program code instructions. Thus processes taught by the discussion above may be performed with program code such as machine-executable instructions that cause a machine that executes these instructions to perform certain functions. In this context, a "machine" may be a machine that converts intermediate form (or "abstract") instructions into processor specific instructions (e.g., an abstract execution environment such as a "virtual machine" (e.g., a Java Virtual Machine), an interpreter, a Common Language Runtime, a high-level language virtual machine, etc.), and/or, electronic circuitry disposed on a semiconductor chip (e.g., "logic circuitry" implemented with transistors) designed to execute instructions such as a general-purpose processor and/or a special-purpose processor. Processes taught by the discussion above may also be performed by (in the alternative to a machine or in combination with a machine) electronic circuitry designed to perform the processes (or a portion thereof) without the execution of program code.

The present invention also relates to an apparatus for performing the operations described herein. This apparatus may be specially constructed for the required purpose, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), RAMs, EPROMs, EEPROMs, magnetic or optical cards, or any type of media suitable for storing electronic instructions, and each coupled to a computer system bus.

A machine readable medium includes any mechanism for storing or transmitting information in a form readable by a machine (e.g., a computer). For example, a machine readable medium includes read only memory ("ROM"); random access memory ("RAM"); magnetic disk storage media; optical storage media; flash memory devices; etc.

An article of manufacture may be used to store program code. An article of manufacture that stores program code may be embodied as, but is not limited to, one or more memories (e.g., one or more flash memories, random access memories (static, dynamic or other)), optical disks, CD-ROMs, DVD ROMs, EPROMs, EEPROMs, magnetic or optical cards or other type of machine-readable media suitable for storing electronic instructions. Program code may also be downloaded from a remote computer (e.g., a server) to a requesting computer (e.g., a client) by way of data signals embodied in a propagation medium (e.g., via a communication link (e.g., a network connection)).

The preceding detailed descriptions are presented in terms of algorithms and symbolic representations of operations on data bits within a computer memory. These algorithmic descriptions and representations are the tools used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be kept in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "receiving," "performing," "analyzing," "determining," "computing," "sending," "creating," "applying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The processes and displays presented herein are not inherently related to any particular computer or other apparatus. Various general-purpose systems may be used with programs in accordance with the teachings herein, or it may prove convenient to construct a more specialized apparatus to perform the operations described. The required structure for a variety of these systems will be evident from the description below. In addition, the present invention is not described with reference to any particular programming language. It will be appreciated that a variety of programming languages may be used to implement the teachings of the invention as described herein.

The foregoing discussion merely describes some exemplary embodiments of the present invention. One skilled in the art will readily recognize from such discussion, the accompanying drawings and the claims that various modifications can be made without departing from the spirit and scope of the invention.

What is claimed is:

1. A non-transitory machine-readable medium having executable instructions to cause one or more processing units to perform a method to update rules for a plurality of entities in a simulation as the simulation is running, the method comprising:
   receiving configuration parameters for the simulation, the configuration parameters including a plurality of rules that control the interactions of the plurality of entities in the simulation;
   performing the simulation for a first plurality of iterations;
   analyzing the simulation results to determine when there is an update for the plurality of rules, wherein the rule update is an update for at least one of the plurality of rules for an interaction potential between a pair of the plurality of the entities that is based on at least a distance between the pair of the plurality of entities;
   when there is an update for the plurality of rules, creating the rule update for the plurality of rules; and
   applying the rule update to the plurality of rules.

2. The non-transitory machine-readable medium of claim 1, further comprising:
   performing the simulation for a second plurality of iterations using the updated plurality of rules.

3. The non-transitory machine-readable medium of claim 1, wherein the analyzing of the simulation comprises:
   determining if a pair of the plurality of entitles are within an interaction distance for this pair for a minimum number of iteration.

4. The non-transitory machine-readable medium of claim 1, wherein the rule update is a new rule adding an attraction potential between the pair of the plurality of entities.

5. The non-transitory machine-readable medium of claim 1, wherein the rule update is selected from the group consisting of an increase to an existing pairwise interaction between the pair of the plurality of entities and a decrease to a pairwise interaction between the pair of the plurality of entities.

6. The non-transitory machine-readable medium of claim 1, wherein the analyzing of the simulation comprises:
   determining if a pair of the plurality of entitles are not within an interaction distance of this pair for a minimum number of iteration.

7. The non-transitory machine-readable medium of claim 1, further comprising:
   receiving experimental data associated with the plurality of rules.

8. The non-transitory machine-readable medium of claim 7, wherein the analyzing of the simulation comprises:
   analyzing the simulation results and experimental data to determine if there is an update for the plurality of rules.

9. A method to update rules for a plurality of entities in a simulation as the simulation is running, the method comprising:
receiving configuration parameters for the simulation, the configuration parameters including a plurality of rules that control the interactions of the plurality of entities in the simulation;
performing the simulation for a first plurality of iterations;
analyzing the simulation results to determine when there is an update for the plurality of rules;
when there is an update for the plurality of rules, creating the rule update for the plurality of rules, wherein the rule update is an update for at least one of the plurality of rules for an interaction potential between a pair of the plurality of the entities that is based on at least a distance between the pair of the plurality of entities; and
applying the rule update to the plurality of rules.

10. The method of claim 9, further comprising:
performing the simulation for a second plurality of iterations using the updated plurality of rules.

11. The method of claim 9, wherein the analyzing of the simulation comprises:
determining if a pair of the plurality of entitles are within an interaction distance for this pair for a minimum number of iteration.

12. The method of claim 9, wherein the rule update is a new rule adding an attraction potential between the pair of the plurality of entities.

13. The method of claim 9, wherein the rule update is selected from the group consisting of an increase to an existing pairwise interaction between the pair of the plurality of entities and a decrease to a pairwise interaction between the pair of the plurality of entities.

14. The method of claim 9, wherein the analyzing of the simulation comprises:
determining if a pair of the plurality of entitles are not within an interaction distance of this pair for a minimum number of iteration.

15. The method of claim 9, further comprising:
receiving experimental data associated with the plurality of rules.

16. The method of claim 15, wherein the analyzing of the simulation comprises:
analyzing the simulation results and experimental data to determine if there is an update for the plurality of rules.

17. A device that updates rules for a plurality of entities in a simulation as the simulation is running, the device comprising:
a processor;
a memory coupled to the processor though a bus; and
a process executed from the memory by the processor that causes the processor to receive configuration parameters for the simulation, the configuration parameters including a plurality of rules that control the interactions of the plurality of entities in the simulation, perform the simulation for a first plurality of iterations, analyze the simulation results to determine when there is an update for the plurality of rules, when there is an update for the plurality of rules, create the rule update for the plurality of rules, and apply the rule update to the plurality of rules, wherein the rule update is an update for at least one of the plurality of rules for an interaction potential between a pair of the plurality of the entities that is based on at least a distance between the pair of the plurality of entities.

18. The device of claim 17, wherein the process further causes the processor to perform the simulation for a second plurality of iterations using the updated plurality of rules.

19. The device of claim 17, wherein the rule update is a new rule adding an attraction potential between the pair of the plurality of entities.

20. The device of claim 17, wherein the rule update is selected from the group consisting of an increase to an existing pairwise interaction between the pair of the plurality of entities and a decrease to a pairwise interaction between the pair of the plurality of entities.

* * * * *